US009169463B2

(12) United States Patent
Hirano et al.

(10) Patent No.: US 9,169,463 B2
(45) Date of Patent: Oct. 27, 2015

(54) STEM CELL FOR THERAPEUTIC USE WHICH IS DERIVED FROM HUMAN MONOCYTE, AND METHOD FOR INDUCING SAME

(75) Inventors: Hisanobu Hirano, Osaka (JP); Yasushi Ohkubo, Osaka (JP); Kenjiro Sasaki, Osaka (JP); Hironobu Ishiyama, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 97 days.

(21) Appl. No.: 13/130,099

(22) PCT Filed: Nov. 19, 2009

(86) PCT No.: PCT/JP2009/069648
§ 371 (c)(1),
(2), (4) Date: May 19, 2011

(87) PCT Pub. No.: WO2010/061781
PCT Pub. Date: Jun. 3, 2010

(65) Prior Publication Data
US 2011/0223143 A1 Sep. 15, 2011

(30) Foreign Application Priority Data
Nov. 25, 2008 (JP) ................................ 2008-299359

(51) Int. Cl.
*C12N 5/0786* (2010.01)
*A61K 35/12* (2015.01)

(52) U.S. Cl.
CPC ............... *C12N 5/0645* (2013.01); *A61K 35/12* (2013.01); *C12N 2500/76* (2013.01); *C12N 2501/22* (2013.01)

(58) Field of Classification Search
CPC ............ C12N 5/0645; C12N 2501/22; C12N 2500/76; A61K 35/12
USPC .......................................... 424/93.7; 435/377
See application file for complete search history.

(56) References Cited

U.S. PATENT DOCUMENTS

| 5,272,138 | A | 12/1993 | Hakomori et al. | |
|---|---|---|---|---|
| 6,084,060 | A * | 7/2000 | Moore | 530/200 |
| 2004/0101962 | A1 | 5/2004 | Kremer et al. | |
| 2004/0209812 | A1 | 10/2004 | Renzi et al. | |
| 2005/0221483 | A1 * | 10/2005 | Kremer et al. | 435/372 |
| 2005/0260748 | A1 * | 11/2005 | Chang et al. | 435/366 |

FOREIGN PATENT DOCUMENTS

| JP | 2006-521405 | 9/2006 |
|---|---|---|
| RU | 2 451 744 C2 | 5/2012 |
| WO | WO 03/083092 | 10/2003 |
| WO | WO 03/0833092 A1 | 10/2003 |
| WO | WO 2008/083233 A2 | 7/2008 |

OTHER PUBLICATIONS

Dresske et al. Multipotent Cells of Monocytic Origin Improve Damaged Heart Function. American Journal of Transplantation 2006; 6: 947-958.*
Resveratrol. Sigma Product Information. 1997, p. 1-2.*
Yohe et al. The major gangliosides of human peripheral blood monocytes/macrophages: absence of ganglio series structures. Glycobiology (2001) 11 (10): 831-841.*
English-language International Search Report from the Japanese Patent Office for International Application No. PCT/JP2009/069648, mailed Dec. 28, 2009.
Zhao, Y., et al., "A Human Peripheral Blood Monocyte-Derived Subset Acts As Pluripotent Stem Cells," Proceedings of the National Academy of Sciences of the United States of America, vol. 100, No. 5, pp. 2426-2431, (2003).
Kuwana, M., et al., "Human Circulating CD14+ Monocytes As a Source of Progenitors That Exhibit Mesenchymal Cell Differentiation," Journal of Leukocyte Biology, vol. 74, pp. 833-845, (2003).
Ceradini, D. J., et al., "Progenitor Cell Trafficking Is Regulated by Hypoxic Gradients Through HIF-1 Induction of SDF-1," Nature Medicine, vol. 10, No. 10, pp. 858-864, (2004).
Ruhnke, M., et al., "Differentiation of in Vitro-Modified Human Peripheral Blood Monocytes Into Hepatocyte-like and Pancreatic Islet-like Cells," Gastroenterology, vol. 128, pp. 1774-1786, (2005).
Li, J., et al., "cDNA Microarray Analysis Reveals Fundamental Differences in the Expression Profiles of Primary Human Monocytes, Monocyte-Derived Macrophages, and Alveolar Macrophages," Journal of Leukocyte Biology, vol. 81, pp. 328-335, (2007).
Folch, J. et al., "A Simple Method for the Isolation and Purification of Total Lipids from Animal Tissues," J. Biol. Chem., vol. 226, pp. 497-509, (1957).
European Patent Office, Communication enclosing the "extended European search report," Jan. 30, 2013, issued in corresponding European patent application No. EP 09 82 9029, 7 pages.
M, Kucia at al.. "A Population of Very Small Embryonic-like (VSEL) CXCR4 'SSEA-l' Oct-4'Stem Cells Identified in Adult Bone Marrow" Leukemia (2005), vol. 20, pp. 857-889.
Alok Chandra Bharti, "Gangliosides derived from a T Cell Lymphoma Inhibit Bone Marrow Cell Proliferation and Differentiation," International Immunopharmacology, vol. 1 (2001) pp. 155-165.
T. Koblas et al., "Isolation and Characterization of Human CXCR4-Positive Pancreatic Cells," article, vol. 53, No. 1, pp. 13-22, Prague, Czech Republic, 2007.
A. Di Martino et al., "Purification of non-infectious ganglioside preparations from scrapie-infected brain tissue," Archives of Virology, 1992, vol. 124, pp. 111-121.

(Continued)

*Primary Examiner* — Taeyoon Kim
(74) *Attorney, Agent, or Firm* — Finnegan, Henderson, Farabow, Garrett & Dunner, L.L.P.

(57) ABSTRACT

The present invention relates to stem cells obtained by culturing monocytes in the presence of (i) M-CSF and (ii) at least one member selected from the group consisting of ganglioside and water-soluble plant-derived extract, thereby dedifferentiating the monocytes; a therapeutic agent for treating damaged cells, tissues or organs; a cell drug agent; a method of producing stem cells, a culture medium for dedifferentiating monocytes; a dedifferentiation inducing agent; a cell drug kit; a kit for producing dedifferentiated cells; and a pharmaceutical composition.

4 Claims, 4 Drawing Sheets

(56) References Cited

OTHER PUBLICATIONS

Lars Svennerholm, Gangliosides—A New Therapeutic Agent Against Stroke and Alzheimer's Disease, Live Sciences, 1994, vol. 5, Nos. 25-26, pp. 2125-2134.

Examination Report dated Jul. 13, 2011 issued in corresponding New Zealand Application No. 592671.

Agriculture Biotechnologies, edited by V.S. Sheveluha, M., "High School", 1998.

Carolei A, et al., "Monosialoganglioside GM1 in Cerebral Ischemia," Cerebrovasc Brain Metab, Rev. 1991, Summer, 3(2), 134-157 (Abstract).

Glick, Bernard R. et al., "Molecular Biotechnology," MIR, 2002, p. 27.

Office Action for Corresponding RU Patent Application No. 2011126165 dated Sep. 11, 2013.

Office Action for Corresponding EP Patent Application No. 09 829 029.9-1402 dated Oct. 10, 2014.

S.E. Karpiak et al., "Reduction of Cerebral Edema With GM1 Ganglioside", Journal of Neuroscience Research, vol. 12, pp. 485-492, 1984.

Yong Man et al., "Effects of Different Dose of Ganglioside on Proliferation and Differentiation of Nerve Stem Cells," Chinese Journal of Clinical Rehabilitaion, Aug. 5, 2004, vol. 8, No. 22, pp. 4634-4635.

Office Action for Corresponding RU Patent Application No. 2011126165 dated Nov. 13, 2014.

Common methods of analysis of medicinal plant material, Ministry of Health of the USSR State Pharmacopoeia of the USSR, 11$^{th}$ edition, Issue 2, Moscow, "Meditsina" 1990.

G.B. Tyukavin, Carrot Biotechnology, Under the editorship and the foreword of the academician RAAS doctor of agricultural sciences, Professor V. F. Pivovarov, Moscow, 2007.

\* cited by examiner

Number of days of culture (day)

1. Sweet potato stem
2. Lotus root stem
3. Ipomoea congesta

1. Sweet potato stem extract
2. SP-Sepharose flow-through fr.
3. Q-Sepharose flow-through fr.
4. Con A agarose flow-through fr.

SEQUENCE LISTING

<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: Primer for Nanog

<400> SEQUENCE: 1
gcttgccttg ctttgaagca                20

<210> SEQ ID NO 2
<211> LENGTH: 20
<212> TYPE: DNA
<213> ORGANISM: Artificial
<220> FEATURE:
<223> OTHER INFORMATION: Primer for Nanog

<400> SEQUENCE: 2
ttcttgactg ggaccttgtc                20

<210> SEQ ID NO 3
<211> LENGTH: 20
<212> TYPE: DNA
<213> ORGANISM: Artificial
<220> FEATURE:
<223> OTHER INFORMATION: primer for Nestin

<400> SEQUENCE: 3
ctctgacctg tcagaagaat                20

<210> SEQ ID NO 4
<211> LENGTH: 20
<212> TYPE: DNA
<213> ORGANISM: Artificial
<220> FEATURE:
<223> OTHER INFORMATION: primer for Nestin

<400> SEQUENCE: 4
gacgctgaca cttacagaat                20

<210> SEQ ID NO 5
<211> LENGTH: 19
<212> TYPE: DNA
<213> ORGANISM: Artificial
<220> FEATURE:
<223> OTHER INFORMATION: primer for Oct3/4

<400> SEQUENCE: 5
gagcaaaacc cggaggagt                19

<210> SEQ ID NO 6
<211> LENGTH: 19
<212> TYPE: DNA
<213> ORGANISM: Artificial
<220> FEATURE:
<223> OTHER INFORMATION: primer for Oct3/4

<400> SEQUENCE: 6
ttctctttcg ggcctgcac                19

<210> SEQ ID NO 7
<211> LENGTH: 20
<212> TYPE: DNA
<213> ORGANISM: Artificial

```
<220> FEATURE:
<223> OTHER INFORMATION: primer for CD117(c-Kit)

<400> SEQUENCE: 7
ccaagtcatt gttggataag                                              20

<210> SEQ ID NO 8
<211> LENGTH: 21
<212> TYPE: DNA
<213> ORGANISM: Artificial
<220> FEATURE:
<223> OTHER INFORMATION: primer for CD117(c-Kit)

<400> SEQUENCE: 8
cttagatgag ttttctttca c                                            21

<210> SEQ ID NO 9
<211> LENGTH: 30
<212> TYPE: DNA
<213> ORGANISM: Artificial
<220> FEATURE:
<223> OTHER INFORMATION: primer for CXCR4

<400> SEQUENCE: 9
atcttcctgc ccaccatcta ctccatcatc                                   30

<210> SEQ ID NO 10
<211> LENGTH: 30
<212> TYPE: DNA
<213> ORGANISM: Artificial
<220> FEATURE:
<223> OTHER INFORMATION: primer for CXCR4

<400> SEQUENCE: 10
atccagacgc caacatagac caccttttca                                   30
```

STEM CELL FOR THERAPEUTIC USE WHICH IS DERIVED FROM HUMAN MONOCYTE, AND METHOD FOR INDUCING SAME

TECHNICAL FIELD

The present invention relates to a method for providing cells for use in cell drugs by quickly dedifferentiating cells that are properly differentiated in a living body. The present invention also relates to an agent for treating diseases related to damaged cells, tissues or organs. The present invention further relates to a cell drug agent, a method of producing stem cells, a culture medium for dedifferentiating monocytes, a dedifferentiation inducing agent, a cell drug kit, a kit for producing dedifferentiated cells, and a pharmaceutical composition, all of which efficiently induce cell dedifferentiation, and stem cells.

BACKGROUND ART

It has been some time since medical procedures, namely regeneration medicine, for replacing cells that have been lost from tissue for some reason have attracted attention as a fundamental treatment for diseases. In recent years, the concept of cell drugs, which aim to regenerate and repair tissue in a disease site via the interaction of intercellular bioactive substances by injecting stem cells or precursor cells of tissue cells, has been further broadened.

In response to these circumstances, there have been many reports that differentiated cells in tissue, e.g., peripheral blood-derived monocytes, dedifferentiate into stem cells when cultured in the presence of specific cytokines.

However, when stem cells or tissue precursor cells, as a cell drug, are administered to a living body, the percentage of cells arriving at the target damaged area is not always high and is not constant. This problematically necessitates the preparation of a large amount of cells. Further, the behavior of cells that are distributed in areas other than the target area has not yet been studied in detail, and there remains a problem of side effects. Moreover, although administration of a large amount of cells is necessary for an enhanced therapeutic effect, it seems difficult to obtain autologous cells in a short period of time.

It has recently become evident that a phenomenon called homing occurs. This is a phenomenon in which SDF1 (stromal cell-derived factor 1) or VEGF (vascular endothelial cell growth factor) is expressed in a damaged area under ischemic conditions; as part of the biological repair system, these factors serve as inducible molecules; and cells expressing receptors corresponding to these inducible molecules are drawn to the damaged area. Receptors for these factors are CXCR4 for SDF1 and VEGFR for VEGF. For example, Non-Patent Document 1 reports that a wound does not heal when SDF1 is blocked in the ischemic area or when CXCR4-expressing cells are removed from the blood.

Fändrich (Non-Patent Document 2), Huberman (Non-Patent Document 3), etc., report techniques of obtaining stem cells with pluripotency from human monocytes by inducing dedifferentiation. These techniques use various cytokines, including M-CSF, for incubation. Each culture method showed that some undifferentiated markers became positive. Additionally, Kuwana et al. (Non-Patent Document 4) reports that multipotential stem cells (MOMC) can be induced from human mononuclear cells using a culture plate to which fibronectin is applied.

CITATION LIST

Non-Patent Document 1: Nat. Med. 2004 August; 10 (8): 858-64
Non-Patent Document 2: Ruhnke M, Fändrich F, "Differentiation of in vitro-modified human peripheral blood monocytes into hepatocyte-like and pancreatic islet-like cells", Gastroenterology, 128 (2005) 1774
Non-Patent Document 3: Yong Zhao, Eliezer Huberman, "A human peripheral blood monocyte-derived subset acts as pluripotent stem cells", PNAS 100 (2003) 2426
Non-Patent Document 4: Kuwana M. et al., "Human circulating CD14+ monocytes as a source of progenitors that exhibit mesenchymal cell differentiation", J. Leukoc. Biol., 74 (2003) 833
Non-Patent Document 5: Folch J., Lees M., Sloane-Stanley G. H., "A simple method for the isolation and purification of total lipids from animal tissues", J. Biol. Chem., 226, 497-509 (1957)

SUMMARY OF INVENTION

Technical Problem

The production of stem cells that are efficiently accessible to a target area has been considered challenging in the field of cell drugs. An object of the present invention is to provide such stem cells, a method for short-term mass production of the stem cells, and a pharmaceutical composition for inducing the stem cells.

Another object of the invention is to provide an agent for treating diseases related to damaged cells, tissues or organs.

Still another object of the invention is to provide a dedifferentiation-inducing culture medium, a dedifferentiation inducing agent, a cell drug kit, a kit for producing dedifferentiated cells, and stem cells.

Solution to Problem

As a solution for the above problems, the present invention found that cultivating peripheral blood monocytes in a short period of time in the presence of a dedifferentiation inducing agent of the present invention produces a large amount of dedifferentiated cells. The present invention also found that direct administration of a pharmaceutical composition of the present invention to a living body is significantly effective to treat damage-related diseases. The present invention further found that administration of at least one member selected from the group consisting of ganglioside and water-soluble plant-derived extract induces dedifferentiation of monocytes into cells capable of recovering damaged tissues or organs, such as stem cells, possibly in cooperation with intravital M-CSF. The present invention can thus provide a therapeutic agent for treating diseases related to damaged cells, tissues or organs.

Specifically, the present invention provides the followings.
Item 1. Stem cells obtained by culturing monocytes in the presence of (i) M-CSF and (ii) at least one member selected from the group consisting of ganglioside and water-soluble plant-derived extract, thereby dedifferentiating the monocytes.
Item 2. The stem cells according to Item 1 wherein an active ingredient of the water-soluble plant-derived extract is sugar or a sugar-containing complex, the active ingredient dedifferentiating the monocytes.
Item 3. The stem cells according to Item 1 wherein an active ingredient of the water-soluble plant-derived extract has a molecular weight of 1000 to 500000, the active ingredient dedifferentiating the monocytes.

Item 4. The stem cells according to Item 1 wherein an active ingredient of the water-soluble plant-derived extract is adsorbed to a Con A column, the active ingredient dedifferentiating the monocytes.

Item 5. The stem cells according to Item 1 wherein an active ingredient of the water-soluble plant-derived extract is adsorbed to an anion exchange resin, the active ingredient dedifferentiating the monocytes.

Item 6. The stem cells according to Item 1, wherein the water-soluble plant-derived extract is a plant-derived Folch-extracted aqueous phase fraction or a purified product thereof.

Item 7. The stem cells according to Item 1, wherein the monocytes are human monocytes.

Item 8. The stem cells according to any one of Items 1 to 7, wherein at least one member of undifferenciated markers Nanog, Nestin, c-Kit, CD9, and Oct3/4 is expressed, and expression of a CXCR4 gene is significant compared with stem cells obtained by culturing monocytes in the sole presence of M-CSF.

Item 9. Stem cells in which at least one member of undifferenciated markers Nanog, Nestin, c-Kit, CD9, and Oct3/4 is expressed, and expression of a CXCR4 gene is significant.

Item 10. A method of producing stem cells, comprising culturing monocytes in the presence of (i) M-CSF and (ii) at least one member selected from the group consisting of ganglioside and water-soluble plant-derived extract.

Item 11. The method according to Item 10 wherein the culture is performed for 7 to 14 days.

Item 12. A culture medium for dedifferentiating monocytes containing (i) M-CSF and (ii) at least one member selected from the group consisting of ganglioside and water-soluble plant-derived extract.

Item 13. A pharmaceutical composition containing the stem cells according to any one of Items 1 to 9 as an active ingredient.

Item 14. A cell drug agent containing the stem cells according to any one of Items 1 to 9 as an active ingredient.

Item 15. A dedifferentiation inducing agent containing (i) M-CSF and (ii) at least one member selected from the group consisting of ganglioside and water-soluble plant-derived extract as active ingredients.

Item 16. An agent for treating diseases related to damaged cells, tissues or organs, containing at least one member selected from the group consisting of ganglioside and water-soluble plant-derived extract as an active ingredient.

Item 17. The agent for treating diseases related to damaged cells, tissues or organs according to Item 16, wherein the diseases are selected from the group consisting of external injuries, inflammatory diseases, damaged bone or cartilage, cardiovascular diseases, neurological disorders, liver diseases, renal diseases, diabetes, atopic dermatitis, and GVHD.

Item 18. The agent for treating diseases related to damaged cells, tissues or organs according to Item 16, wherein the diseases are selected from the group consisting of external injuries, pancreatitis, radiation damage, dermatomyositis, multiple myositis, necrotic fasciitis, chronic bronchitis, bone fracture, osteoporosis, osteocartilaginous fracture, osteochondritis, dilated cardiomyopathy, myocardial infarction, ischaemic cardiomyopathy, cardiac insufficiency, myocardium hypertrophy, congestive heart failure, restenosis, arrhythmia, atherosclerosis, vasculitis, peripheral neuropathy, neuropathic pain, cerebral apoplexy, encephalitis, meningitis, diabetic neuropathy, attention deficit disorder, autism, Alzheimer disease, Parkinson's disease, Creutzfeldt-Jakob disease, external injuries or ischemia of the brain or spine, liver cirrhosis, chronic hepatitis, chronic renal failure, glomerular nephritis, kidney ischemia, diabetes, atopic dermatitis, and GVHD.

Item 19. A cell drug kit containing at least the stem cells according to any one of Items 1 to 9 as an essential ingredient.

Item 20. A kit for producing dedifferentiated cells, comprising (i) M-CSF and (ii) at least one member selected from the group consisting of ganglioside and water-soluble plant-derived extract as essential ingredients.

Item 21. The kit according to Item 20, further comprising monocytes as an component.

Item 22. The stem cells, the method of producing stem cells, the culture medium for dedifferentiating monocytes, the cell drug agent, the agent for treating diseases, the dedifferentiation inducing agent, the cell drug kit, or the kit for producing dedifferentiated cells according to Item 1, 2, 3, 4, 5, 6, 7, 8, 9, 10, 11, 12, 13, 14, 15, 16, 17, 18, 19, 20 or 21 wherein ganglioside is at least one member selected from the group consisting of GD1a, GD1b, GD2, GD3, GM1, GM2, GM3, GT1b, and GQ1b.

Advantageous Effects of Invention

Using monocytes, the present invention provides a short-period mass production of stem cells accessible to damaged tissues. The present invention also provides an agent for inducing stem cells. The present invention is thus expected to contribute to the field of cell drugs.

Furthermore, it has been proved that ganglioside and water-soluble plant-derived extract, such as a plant-derived Folch-extracted aqueous phase fraction or a purified product thereof, serve as a drug for treating diseases related to damaged cells, tissues or organs.

BEST MODE FOR CARRYING OUT THE INVENTION

Figure 1:
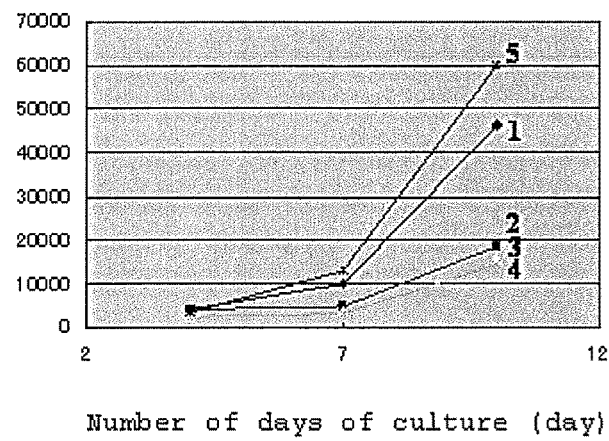
FIG. 1 shows the growth curves of stem cells induced from monocytes by culturing in media 1 to 5.

The present invention uses monocytes, such as peripheral blood monocytes, as the cells subjected to dedifferentiation.

The present invention uses mammalian derived monocytes, obtained from humans, equines, bovines, apes, chimpanzees, swine, sheep, rabbits, mice, rats, canines, felines and like mammalians. Among these, humans, apes, chimpanzees and like primates are preferable. Human monocytes are particularly preferable. The monocytes are derived from bone marrow or blood. It is preferable to use blood-derived monocytes, particularly, peripheral blood-derived monocytes.

A method for separating monocytes from sample blood or the like is publicly known. For example, there is a method of first separating mononuclear cells from blood using a blood cell separation solution "Lymphoprep™" (Cosmo Bio Co. Ltd.), and treating the obtained mononuclear cells with antibody magnetic beads (Miltenyi Biotec) capable of recognizing the surface antigen of CD14, thereby separating the target monocytes. The mononuclear cells may also be directly used as a source for obtaining the monocyte of the present invention.

Human monocytes may be selected from products that are commercially available, such as PT038 (Lonza).

The present invention dedifferentiates monocytes into stem cells, and the resulting cells are proliferated before being placed back into a test subject such as a person. In this case, the monocytes are taken from the patient, and therefore, it is necessary to obtain as many stem cells as possible from the minimum amount of monocytes. The present invention has an advantage of dedifferentiating stem cells from monocytes with high proliferation efficiency, thereby producing a large amount of stem cells out of a small amount of monocytes.

Examples of the monocytes include monocyte-type cells (monocytes, mononuclear cells, monoblasts) having an M-CSF receptor (c-fms). Since only the monocytes proliferate when both the monocytes and mononuclear cells are used at the same time, the present invention allows for the use of mononuclear cells as the dedifferentiated cells, in addition to the monocytes.

In the present specification, "stem cell" denotes a cell expressing an undifferentiated marker and having an autoreproductive property. By using monocytes, a large amount of stem cells of the present invention may be obtained. The stem cells of the present invention can induce differentiation and preferably have a pluripotent differentiation property. The stem cells obtained in the present invention are CD14 and CD45 positive.

The stem cells of the present invention are characterized by significant expression of CXCR4 genes; it is also characterized in that at least one member, preferably at least two members, more preferably at least three members, further preferably at least four members, particularly preferably all members of Nanog, Nestin, c-Kit, CD9 and Oct3/4 are expressed.

In a preferred form of the stem cell of the present invention, the CXCR4 gene is more significantly expressed than that in stem cells obtained by cultivating monocytes in the sole presence of M-CSF, and at least one member, preferably at least two members, more preferably at least three members, further preferably at least four members, particularly preferably all of the five members of Nanog, Nestin, c-Kit, CD9 and Oct3/4 are expressed.

The following are features of the stem cells of the present invention in a more preferable embodiment:
(i) CXCR4 gene is more significantly expressed than that in the stem cells obtained by cultivating monocytes in the sole presence of M-CSF monocytes;
(ii) c-Kit is expressed; and
(iii) at least one undifferentiated marker selected from the group consisting of Nanog, Nestin, CD9 and Oct3/4 is expressed.

The feature that differentiates the monocytes derived stem cells of the present invention from other dedifferentiated stem cells is significant expression of the CXCR4 gene, which is involved in cell homing. In the stem cells of the present invention, CXCR4 genes are more significantly expressed than those in stem cells obtained by cultivating monocytes in the sole presence of M-CSF. For example, in a preferred embodiment of the stem cells of the present invention, the amount of CXCR4 gene expression assayed by RT-PCR or the like is more than three or four times greater than the amount of expression resulting from cultivating monocytes in the sole presence of M-CSF, or in the presence of M-CSF+ IL-3, M-CSF+IL-6&LIF etc. Moreover, in a preferred embodiment of the stem cells of the present invention, CXCR4 genes are more significantly expressed than those in bone marrow-derived mesenchymal stem cells; more specifically, the amount of CXCR4 gene expression assayed by RT-PCR or the like is more than two or three times greater than that in bone marrow.

The monocyte derived stem cells of the present invention are characterized by, as with the other dedifferentiated stem cells, the expression of c-Kit, which is a stem cell marker.

It is known that SDF1, the ligand for the CXCR4 receptor, is expressed in tissues that are damaged as a result of bone fractures and circulatory diseases, in the damaged portions of neural tissue, or the like. Therefore, the cells provide a further improved cell homing effect with respect to damaged areas when serving as a cell drug.

The stem cells obtained by the present invention may be used for treating diseases by administering/injecting them into affected areas. Before injection, it is preferable to cultivate the stem cells in an appropriate culture medium to proliferate the cells. Then, the cells are directly administered/ injected into the affected areas. The stem cells may be cultivated in a general cell culture medium; however, it is preferable to culture the stem cells in the dedifferentiation inducing culture medium of the present invention.

According to one embodiment of the present invention, the stem cells of the present invention can be used for treating external injuries, inflammatory disease (pancreatitis, radiation damage, dermatomyositis, multiple myositis, necrotic fasciitis, chronic bronchitis), damaged bone or cartilage (bone fracture, osteoporosis, osteocartilaginous fracture, osteochondritis), cardiovascular diseases (e.g., dilated cardiomyopathy, myocardial infarction, ischaemic cardiomyopathy, cardiac insufficiency, myocardium hypertrophy, congestive heart failure, restenosis, arrhythmia, atherosclerosis, vasculitis, etc.), neurological disorders (e.g., peripheral neuropathy, neuropathic pain, cerebral apoplexy, encephalitis, meningitis, diabetic neuropathy, attention deficit disorder, autism, Alzheimer disease, Parkinson's disease, Creutzfeldt-Jakob disease, external injuries or ischemia of the brain or spine, etc.), liver diseases (liver cirrhosis, chronic hepatitis), renal diseases (chronic renal failure, glomerular nephritis, kidney ischemia etc.), diabetes, atopic dermatitis, GVHD or the like.

The dedifferentiated stem cells of the present invention were deposited with the International Patent Organism Depositary of the National Institute of Advanced Industrial Science and Technology (Central 6, 1-1, Higashi 1-chome Tsukuba-shi, Ibaraki-ken 305-8566 Japan) on Sep. 30, 2009, under accession number ABP-11184.

As mentioned above, the monocytes are converted into stem cells by culturing the monocytes in the presence of (i) M-CSF and (ii) at least one member selected from the group consisting of ganglioside and water-soluble plant-derived extract.

In the present specification, "water-soluble plant-derived extract" denotes an extract of the entire plant or a part (for example, leaves, stems, subterranean stems, rhizomes, tubers, vines, roots, flowers, buds, petals, ovaries, fruits, pods, capsules, seeds, fibers, ovules, etc.) of a plant. Examples of the extractants include water, an aqueous solvent (for example, aqueous alcohol such as aqueous methanol, aqueous ethanol, or aqueous propanol; aqueous THF; aqueous acetone), and polar solvents such as DMF, DMSO, or dimethylacetamide. The "water-soluble plant-derived extract" is a substance extracted from such a solvent, i.e., water, an aqueous solvent, or a polar solvent capable of dissolving polar substance in high amount. The water-soluble plant-derived extract can be obtained as follows. First, a plant is extracted using chlorinated hydrocarbons such as chloroform or methylene chloride; alcohols such as methanol, ethanol or propanol; aromatic hydrocarbons such as benzene or toluene; esters such as ethyl acetate; ethers such as THF or diethyl ether; ketones such as acetone and methyl ethyl ketone; aliphatic or alicyclic hydrocarbons such as hexane or cyclohexane. Thereafter, the plant extract is treated with water or a aqueous solvent to obtain the target water-soluble substance. The water-soluble substance thus obtained using water, an aqueous solvent or a polar solvent may be, as required, further treated with chlorinated hydrocarbons such as chloroform or methylene chloride; aromatic hydrocarbons such as benzene or toluene; esters such as ethyl acetate; ethers such as THF or diethyl ether; aliphatic or alicyclic hydrocarbons such as hexane or cyclohexane, so as to wash off the lipophilic component. The water-soluble plant-derived extract is preferably a plant-derived Folch-extracted aqueous phase fraction or a purified product thereof.

The Folch extract denotes a fraction remained in the aqueous phase as a result of a plant extraction process using a solvent of chloroform:methanol=2:1 and washing the mixed solvent with water. Chloroform may instead be other chlorinated hydrocarbons, such as methylene chloride, carbon tetrachloride, or 1,2-dichloroethane. Methanol may instead be lower alcohols, such as ethanol, n-propanol, isopropanol, or butanol. The proportion of chlorinated hydrocarbon to alcohol is not limited to 2:1. A wide range of proportions can be used. Here, the mixed solvent of chlorinated hydrocarbon and alcohol has a high dissolution property, thereby facilitating the extraction. The proportion of chlorinated hydrocarbon to alcohol is preferably set to a value that can ensure separation into an aqueous phase and an organic phase when water is added, thereby extracting the active substance in the aqueous phase. When the phase is not divided by addition of water, an organic solvent is added to separate the solvent into two layers. In the present specification, the aqueous phase resulting from the separation into two layers by adding water is called a "plant-derived Folch-extracted aqueous phase fraction". An aqueous phase fraction extracted by a different method is also included in the range of "plant-derived Folch-extracted aqueous phase fraction", as long as it has the same active substance.

The water-soluble plant-derived extract of the present invention contains a glycolipid-like substance (containing one or both of glycolipid and sugar) as an active ingredient. Since this glycolipid-like substance has a low solubility to an organic solvent, the water-soluble plant-derived extract is preferably isolated as an aqueous phase fraction. Further, the water-soluble plant-derived extract can be further purified using various kinds of chromatography such as ion exchange chromatography or affinity chromatography. The purified product may also be used as the active ingredient.

The active ingredient in the water-soluble plant extract may only be composed of sugar or may contain both sugar and other components (lipids etc.). Examples of sugar components include glucose, arabinose, xylose, ribose, rhamnose, fucose, deoxyribose, mannose, fructose, galactose, maltose, lactose, cellobiose, sucrose, trehalose, raffinose, melibiose, maltotriose, melezitose, turanose, glucuronic acid, galacturonic acid, mannuronic acid, iduronic acid, glucosamine, galactosamine, mannosamine, N-acetylglucosamine, N-acetylgalactosamine, N-acetylmannosamine, neuraminic acid, N-acetylneuraminic acid, and the like. These may be sulfated. It is preferred that these are present in the form of oligosaccharides, polysaccharides, glycosides, or glycolipids. Specific examples of polysaccharides include glycosaminoglycan, $\alpha$-glucan, $\beta$-glucan, levan, fructan, galactan, mannan, xylan, arabinan, pectic acid, alginic acid, pectic substances, guaran, sulfated polysaccharide, polysaccharide in which one or more kinds of sugar residues are linked, polysaccharides formed of repeating units of one or more members of the above sugar residues, and polysaccharide in which plural sugar residues are intricately linked. It is preferable that the water-soluble plant extract is treated with a cation exchange resin after being extracted. In one embodiment, the water-soluble plant extract of the present invention preferably contains a component that is adsorbed to an anion exchange resin (the component having an anionic group in water) as an active ingredient. In another embodiment, the water-soluble plant extract of the present invention preferably contains a component that binds to Con A agarose as an active ingredient. In a preferred embodiment of the present invention, the water-soluble plant extract is adsorbed to an anion exchange resin and contains a component that binds to Con A agarose as an active ingredient. As the active ingredient binding to agarose Con A, polysaccharides or sugars (including sugar-containing complexes such as glycolipids) containing a glucose residue and/or mannose residue, particularly a mannose residue, are preferred. In a preferred embodiment, the water-soluble plant extract contains a component having a sugar residue and being soluble in cold water or hot water (extractable). The component is preferably a polysaccharide or sugar-containing complex in which the lower limit of the molecular weight is about 500, 1000, 2000, 3000, 4000, or 5000, and the upper limit is about 500000, 300000, 200000, 100000, 80000, 60000, 50000, 40000, 30000, or 20000.

The induction into stem cells can be performed by cultivating the monocytes in the presence of at least one member selected from the group consisting of ganglioside and water-soluble plant-derived extract.

Since M-CSF already exists in a living organism (e.g., in the human body), one member selected from the group consisting of ganglioside and water-soluble plant-derived extract can serve as an inducer for causing a conversion from monocytes to stem cells. The stem cells arrive at the disease area, and thereby serve as a therapeutic agent for various kinds of diseases. The therapeutic agent containing, as an active ingredient, at least one member selected from the group consisting of ganglioside and water-soluble plant-derived extract is effective for treating external injuries, inflammatory disease (pancreatitis, radiation damage, dermatomyositis, multiple myositis, necrotic fasciitis, chronic bronchitis), damaged bone or cartilage (bone fracture, osteoporosis, osteocartilaginous fractures, osteochondritis), cardiovascular diseases (e.g., dilated cardiomyopathy, myocardial infarction, ischaemic cardiomyopathy, cardiac insufficiency, myocardium hypertrophy, congestive heart failure, restenosis, arrhythmia, atherosclerosis, vasculitis, etc.), neurological disorders (e.g., peripheral neuropathy, neuropathic pain, cerebral apoplexy, encephalitis, meningitis, diabetic neuropathy, attention deficit disorder, autism, Alzheimer disease, Parkinson's disease, Creutzfeldt-Jakob disease, external injuries or ischemia of the brain or spine, etc.), liver diseases (liver cirrhosis, chronic hepatitis), renal diseases (chronic renal failure, glomerular nephritis, kidney ischemia etc.), diabetes, atopic dermatitis, GVHD or the like.

The effective dosage of the therapeutic agent containing at least one member selected from the group consisting of ganglioside and water-soluble plant-derived extract as an active ingredient depends on, for example, the usage, the age and gender of the patient, the severity of disease or like conditions. Typically, the amount of the active ingredient used is, for an adult, about 0.0001 to 100 mg, preferably about 0.001 to 10 mg, and more preferably about 0.01 to 5 mg with respect to per kg of the body weight. The dosage of the therapeutic agent per day may be divided from 1 to 4 times.

The "plant-derived Folch-extracted aqueous phase fraction" includes a wide range of plant extracts obtained by similar methods. In addition, the active ingredient of the water-soluble plant-derived extract containing the plant-derived Folch-extracted aqueous phase fraction is combinable with anion exchange resins and Con A agarose; and its activity may increase by passing through a cation exchange resin.

When actually used as a medicinal preparation, the therapeutic agent or pharmaceutical composition of the present invention may be formed into a general dosage form by using a pharmaceutical carrier, together with an active ingredient that contains at least one member selected from the group consisting of ganglioside and water-soluble plant-derived extract, and M-CSF as required. The therapeutic carrier is selected depending on the desired drug form, dosage, and method of administration. Examples of therapeutic carriers include various diluents and fillers, such as bulking agents, extenders, binders, moisturizers, disintegrants, surface-active agents, lubricants, etc.

The dosage form of the present invention may be selected from various forms depending on the purpose of treatment. Typical examples of the dosage forms include tablets, pills, powders, liquids, solutions, suspensions, emulsions, granules, capsules, suppositories, injections (liquids, suspensions, etc.), ointments, etc. The drug is prepared into an appropriate form by a general method using a suitable carrier. The tablet may be a tablet having a general coating, such as sugar-coated tablets, gelatin-coated tablets, enteric tablets, film-coated tablets, double-layered tablets or multi-layered tablets, etc. When the drugs of present invention are prepared as injections in the form of a liquid, emulsion, or suspension, the drug is preferably sterilized, and is preferably isotonic to the blood. Therefore, the pharmaceutical composition of the present invention may contain salt, glucose, or glycerol in a quantity sufficient to prepare an isotonic solution. The pharmaceutical composition of the present invention may also contain a general solubilizing agent, buffer, soothing agent, etc. Furthermore, the pharmaceutical composition of the present invention may also contain a colorant, preservative, perfume, flavor agent, sweetening agent, etc., or other medications. When administering both M-CSF and the at least one member selected from the group consisting of ganglioside and water-soluble plant-derived extract, they may be administered simultaneously or separately.

The at least one member selected from the group consisting of ganglioside and water-soluble plant-derived extract may be ingested in the form of food, for example, drinks, bars (supplement bars), etc. Such a food composition can be prepared in accordance with a general method using other appropriate publicly-known food materials (raw materials) excipients, diluents, etc.

The dedifferentiated stem cells may be obtained by inducing dedifferentiation by way of cultivating the above cell material in the coexistence of (i) M-CSF and (ii) at least one member selected from the group consisting of ganglioside and water-soluble plant-derived extract for a predetermined period.

There are membrane-bound M-CSF whose molecular weight is approximately 22000, and secretory M-CSF whose molecular weight is approximately 42000. With a disulfide bond, their molecular weight become approximately 45000 (dimer of 22000) and approximately 85000 (dimer of 42000), respectively. A high molecular weight type M-CSF in which proteoglycan is further bonded with an 85 kDa also exists. Any of these different types of M-CSF may be used; however, the secretory M-CSF whose molecular weight is approximately 42000 and the M-CSF whose molecular weight is approximately 85000 (dimer of 42000), and the high molecular weight type M-CSF in which proteoglycan is further bonded with the 85 kDa are preferred. M-CSF is preferably derived from humans, equines, bovines, apes, chimpanzees, swine, sheep, rabbits, mice, rats, canines, felines and like mammalians. Among them, humans, apes, chimpanzees and like primates are preferable. Human monocytes are particularly preferable. M-CSF may be obtained by purifying a natural product; however, recombinant M-CSF is preferable. For example, it is possible to use an *E. coli*-expressed recombinant with no sugar chain because it is known that M-CSF has a similar specific activity to a natural product when it has the amino acids at least from the N-terminus to the 153th.

The ganglioside is not particularly limited as long as it is selected from the following list including GM1, GD1a, GT1b, etc. A plurality of these gangliosides may be combined. Further, a plant-derived extract (plant-derived glycolipid-like substance) may also significantly induce dedifferentiation. An animal tissue-derived extract (animal-derived glycolipid-like substance) may also be used. The extract can be produced under general conditions for extracting a glycolipid-like substance. The active ingredient of the drug of the present invention is ganglioside or water-soluble plant-derived extract. Any plant-derived extracts or animal tissue-derived extracts containing ganglioside or water-soluble plant-derived extract may be used. For example, ganglioside is abundantly contained in the brain/nerve tissue of an animal, and the extracts derived from the brain and the nerve tissues of an animal can be used as ganglioside. The extracted ganglioside may be purified. Insofar as the fraction contains ganglioside, the degree of purification may be varied. Examples of natural extract fractions include a Folch-extracted (Non-Patent Literature 5) aqueous phase fraction. Preferable examples of animals include mammals (bovines, swine, rabbits, sheep, horses, etc.), and a ganglioside from swine brain or nerve tissues are particularly preferable. A ganglioside derived from the milk of mammals, such as cow's milk, may also be used.

Preferable examples of gangliosides or the water-soluble plant-derived extracts to be used as the material of glycolipid-like substance includes sweet potato, *Ipomea Batatas* sp, morning-glory, swamp morning-glory, Ivy-leaved morning glory, fingerleaf morning glory, cardinal climber, blue morning glory, *Ipomoea congesta*, and like Convolvulaceaes; *Nelumbo nucifera* (lotus root), *Nelumbo lutea*, and like Lotuses; *Solanum americanum, Solanum lycopersicum, Solanum mammosum, Solanum melongena, Solanum nigrum, Solanum tuberosum, Capsicum annuum, Capsicum frutescens, Datura metel, Datura meteloides, Datura stramonium, Brugmansia arborea, Brugmansia suaveolens, Physalis alkekengi* var. *franchetii, P. japonicum, Petunia×hybrida* and like *Solanaceouses*. Apart from the above examples, a wide range of gangliosides or water-soluble plant-derived extracts having a glycolipid may be used. The plant may be leaves, stems, subterranean stems, rhizomes, tubers, vines, roots, flowers, buds, petals, ovaries, fruits, pods, capsules, seeds, fibers, ovules, herbs, etc. The extract may be derived from any of these portions.

For example, the corm portion of potatoes or sweet potatoes may be used, in addition to other portions of potatoes or sweet potato, such as the leaves, stems, subterranean stems, rhizomes, tubers, vines, roots, flowers, buds, petals, ovaries, fruits, pods, capsules, seeds, fibers, ovules, herbs etc.

For example, it is possible to use a transgenic plant which is processed either to introduce necessary genes or to knock out unnecessary genes so as to increase the production of ganglioside or glycolipid-like substances.

"Ganglioside" is a general name of a glycosphingolipid having a sialic acid, such as GD1a, GD1b, GD2, GD3, GM1, GM2, GM3, GT1b, or GQ1b. These gangliosides have the following structures.

GD1a=aNeu5Ac(2-3)bDGalp(1-3)bDGalNAc(1-4)
[aNeu5Ac(2-3)]bDGalp(1-4)bDGlcp(1-1)Cer
GD1b=bDGalp(1-3)bDGalNAc(1-4)[aNeu5Ac(2-8)
aNeu5Ac(2-3)]bDGalp(1-4)bDGlcp(1-1)Cer
GD2=bDGalpNAc(1-4)[aNeu5Ac(2-8)aNeu5Ac(2-3)]bD-
Galp(1-4)bDGlcp(1-1)Cer
GD3=aNeu5Ac(2-8)aNeu5Ac(2-3)bDGalp(1-4)bDGlcp(1-1)Cer
GM1=bDGalp(1-3)bDGalNAc[aNeu5Ac(2-3)]bDGalp(1-4)
bDGlcp(1-1)Cer
GM2=bDGalpNAc(1-4)[aNeu5Ac(2-3)]bDGalp(1-4)bDG-
lcp(1-1)Cer
GM3=aNeu5Ac(2-3)bDGalp(1-4)bDGlcp(1-1)Cer
GT1b=aNeu5Ac(2-3)bDGalp(1-3)bDGalNAc(1-4)
[aNeu5Ac(2-8)aNeu5Ac(2-3)]bDGalp(1-4)bDGlcp(1-1)Cer
GQ1b=aNeu5Ac(2-8)aNeu5Ac(2-3)bDGalp(1-3)
bDGalNAc(1-4)[aNeu5Ac(2-8)aNeu5Ac(2-3)]bDGalp(1-4)bDGlcp(1-1)Cer
aNeu5Ac=5-acetyl-α-neuraminic acid
aNeu5Ac9Ac=5,9-diacetyl-α-neuraminic acid
bDGalp=β-D-galactopyranose
bDGalpNAc=N-acetyl-β-D-galactopyranose
bDGlcp=β-D-glucopyranose
Cer=ceramide (general N-acylated sphingoid)

Any culture media for mammalians may be used. For example, the culture may be performed using a medium such as RPMI 1640, DMEM, Eagle MEM, αMEM, IMEM, or M199 containing, for example, approximately 1 to 20% of serum component such as FBS, FCS, CS, or HS. The culture is preferably performed with, but not limited to, a DMEM medium containing approximately 10% of FBS. A serum-free culture, such as Ultra CULTURE™ (medium for mammalian cell types), may also be used. The serum-free culture medium is not particularly limited.

The dedifferentiated stem cells can be obtained by cultivating monocytes in a medium containing (i) M-CSF and (ii) at least one member selected from the group consisting of ganglioside and water-soluble plant-derived extract at 37° C. for about 7 to 14 days in the presence of 5% $CO_2$. During this culture period, dedifferentiation proceeds, and the specific stem cells of the present invention expressing an undifferenciated marker are obtained. Further, during this culture period, the expression of the CXCR4 gene, which is a feature of the stem cells of the present invention, significantly increases. Even if the culture period is extended, the stem cells of the present invention can be obtained insofar as there is a significant level of CXCR4 gene expression.

When the cell material is cultured under such conditions, the final number of the obtained stem cells is approximately five times the number of those obtained by a culture using only M-CSF or a combination with other cytokines.

It is possible to use a covalent bond or a noncovalent bond complex of M-CSF and at least one member selected from the group consisting of ganglioside and water-soluble plant-derived extract, as a dedifferentiation inducing agent.

Heretofore, some reports have shown stem cell production by culturing monocytes using only M-CSF. In contrast, the present invention combines (i) M-CSF and (ii) at least one member selected from the group consisting of ganglioside and water-soluble plant-derived extract to obtain stem cells having particularly significant expression of CXCR4 gene. The culture is performed using M-CSF at a concentration of 5-100 ng/ml, more preferably 25 ng/ml. The ganglioside may be a mixture of extracts derived from plants or animals, a material obtained by purifying a natural product containing ganglioside, or a chemical composition.

The ganglioside can be contained in a culture medium at a final concentration of about 1-100 µg/ml. The water-soluble plant-derived extract can be contained in a culture medium at a final concentration of about 0.1-100 µg/ml.

The final concentration of the at least one member selected from the group consisting of ganglioside and water-soluble plant-derived extract is about 1-100 µg/ml. In the present specification, "ganglioside" denotes an individual ganglioside, such as GD1a, GD1b, GD2, GD3, GM1, GM2, GM3, GT1b, or GQ1b, or a mixture of these gangliosides. The "ganglioside content" denotes the gross content when multiple gangliosides are used.

Kit

The present invention also provides a cell drug kit, which contains the stem cells of the present invention as an essential ingredient; and a dedifferentiated cell producing kit, which contains (i) M-CSF and (ii) ganglioside or water-soluble plant-derived extract as essential ingredients.

The cell drug kit contains the monocyte-derived stem cells of the present invention, and, as required, a culture medium containing (i) M-CSF and (ii) at least one member selected from the group consisting of ganglioside and water-soluble plant-derived extract, a culture container, etc. The kit may be an injection syringe filled with the monocyte-derived stem cells.

The number of the monocyte-derived stem cells in the cell drug kit is, for example, about $1\times10^4$ to $1\times10^7$ per kit.

The dedifferentiated cell producing kit of the present invention contains (i) M-CSF and (ii) at least one member selected from the group consisting of ganglioside and water-soluble plant-derived extract; it further contains, as required, a cell culture medium, a culture containers, monocytes etc.

INDUSTRIAL APPLICABILITY

Technical Field to which the Invention can be Applied

The present invention is applicable to all fields to which stem cells are applied, particularly to the cell drug field, which is attracting attention in recent years. When applied to this field, the cells must be produced and provided within a short period. Further, considering immunologic rejection, it is important to produce the dedifferentiated stem cells from cells taken from a patient's body and place the produced stem cells back into the body of the same patient for the sake of security. Therefore, it is important to produce a certain amount of stem cells within a short period after the cell material is taken from the patient's body. The present invention is significant in this regard.

One embodiment of the present invention is intravenous administration of dedifferentiated cells.

The cells may be administered to the patient by a general method after the target cells are obtained by the culture. For example, after the trypsin treatment, the cells are collected by centrifugation, and dispersed in an appropriate isotonic solution before being administered intravenously. Further, it is possible to add an appropriate pharmaceutically acceptable carrier to stabilize the cells. When there is a time interval between the isolation of the cells from the culture solution and the administration of the cultured cells, the cells may be conserved in a general method at −80° C. or in the presence of liquid nitrogen. More preferably, the cells are collected to be used for the target treatment 7 to 14 days after the beginning of the culture for dedifferentiating monocytes and then immediately used for the target treatment, because it is likely that the expression level of CXCR4 gene is greatest during this period. Accordingly, the usage period of the cells may be determined depending on the expression level of the marker gene and not limited to the culture period.

Technical Field to which the Therapeutic Agent/Medicinal Component can be Applied The present invention administers at least one member selected from the group consisting of ganglioside and water-soluble plant-derived extract, and, as required, M-CSF, to mammals, such as humans, thereby treating various diseases, such as external injuries, inflammatory diseases, damaged bone or cartilage, cardiovascular diseases, neurological disorders, liver diseases and renal diseases, diabetes, atopic dermatitis, or GVHD. The at least one member selected from the group consisting of ganglioside and water-soluble plant-derived extract serve to dedifferentiate the monocytes of the test subject into stem cells capable of recovering the diseases. The stem cells are moved to the disease area and function as a therapeutic agent. Otherwise, at least one member selected from the group consisting of ganglioside and a plant-derived Folch-extracted aqueous phase fraction can directly or indirectly acts on cells other than monocytes.

Usage as a Kit

The dedifferentiated stem cells produced using the dedifferentiation inducing agent may be used as a kit after being subjected to an appropriate preservation treatment.

Similarly, the dedifferentiation inducing agent may be used as a kit which contains the agent as the essential ingredient.

The following describes the examples of the present invention to more specifically disclose the invention. The present invention is, however, not limited to the examples.

EXAMPLES

The present invention is explained in more detail below on the basis of examples. However, the present invention is not limited to these examples.

Example 1

In accordance with the present invention, human monocytes (PT038; LONZA) were cultured with the addition of the following additives 1 to 5 to a basal culture medium (concentrations are expressed as the final concentration; hereinafter refereed to as "FC"). FIG. 1 shows the results. The vertical axis of FIG. 1 indicates the number of viable cells, and the horizontal axis indicates the number of days of culture. The results demonstrate that the monocyte-derived stem cells of the present invention have a very high proliferative activity compared to those obtained by the techniques reported by Fändrich, Huberman, etc.

Additive 1: M-CSF (FC: 25 ng/ml)+gangliosides (Bovine Brain GD1a; SIGMA) (FC: 100 µg/ml)

Additive 2: M-CSF (FC: 5 ng/ml)+IL-3 (FC: 0.5 ng/ml) (Non-Patent Document 2)

Additive 3: M-CSF (FC: 25 ng/ml)+IL-6 (FC: 20 ng/ml) & LIF (FC: 1000 unit/ml) (Non-Patent Document 3)

Additive 4: M-CSF (FC: 25 ng/ml)

Additive 5: M-CSF (FC: 25 ng/ml)+glycolipid (prepared by dissolving a Folch-extracted aqueous phase fraction obtained from 1 g of plant (sweet potato) on a dry weight basis in 500 ml of culture medium)

The Folch-extracted aqueous phase fraction used in additive 5 was prepared in the following manner. Freeze-dried cells (sweet potato tissue) were thoroughly homogenized in a suitable amount of a physiological saline solution, and then vigorously mixed with an equivalent amount of chloroform-methanol solution (2:1). After the mixture was separated by centrifugation into an organic solvent phase, modified protein phase, and aqueous phase, an extract in the water-soluble fraction of the upper layer was used.

Adding all the additives to DMEM (20% Fetal Bovine Serum), a culture of human monocytes was started at a concentration of $1.5 \times 10^5$ cells/ml (200 µl/well, 96-well plate). The viable cell count was quantified using Promega's CellTiter-Glo™ Luminescent Cell Viability Assay. More specifically, the wells were washed with a physiological saline solution three times every culture day to remove unattached cells, and then the attached and grown cells were quantified.

Meanwhile, the gene expression levels of stem cells obtained by the culture methods according to the present invention and prior art were analyzed by RT-PCR. A culture of human monocytes was started under the above conditions and at a concentration of $1.5 \times 10^5$ cells/ml (6 ml/dish, 6 cm in diameter). On the 14th day, mRNA was collected using the Micro Fast Track 2.0 Kit (Invitrogen). Subsequently, expression level analysis was performed by RT-PCR. The items and the sequence information of the primers are as follows:

```
Nanog
                                          (SEQ ID NO: 1)
   F 5'-GCTTGCCTTGCTTTGAAGCA-3'
                                          (SEQ ID NO: 2)
   R 5'-TTCTTGACTGGGACCTTGTC-3'

Nestin
                                          (SEQ ID NO: 3)
   F 5'-CTCTGACCTGTCAGAAGAAT-3'
                                          (SEQ ID NO: 4)
   R 5'-GACGCTGACACTTACAGAAT-3'

Oct3/4
                                          (SEQ ID NO: 5)
   F 5'-GAGCAAAACCCGGAGGAGT-3'
                                          (SEQ ID NO: 6)
   R 5'-TTCTCTTTCGGGCCTGCAC-3' c-Kit
                                          (SEQ ID NO: 7)
   F 5'-CCAAGTCATTGTTGGATAAG-3'
                                          (SEQ ID NO: 8)
   R 5'-CTTAGATGAGTTTTCTTTCAC-3'

CXCR4
                                          (SEQ ID NO: 9)
   F 5'-ATCTTCCTGCCCACCATCTACTCCATCATC-3'
                                         (SEQ ID NO: 10)
   R 5'-ATCCAGACGCCAACATAGACCACCTTTTCA-3'
```

Lane structure (concentrations are expressed as the final concentration; hereinafter refereed to as "FC")

1: M-CSF (FC: 25 ng/ml)+gangliosides (Bovine Brain GD1a; SIGMA) (FC: 100 µg/ml)

2: M-CSF (FC: 5 ng/ml)+IL-3 (FC: 0.5 ng/ml) (Non-Patent Document 2)

3: M-CSF (FC: 25 ng/ml)+IL-6 (FC: 20 ng/ml)+LIF (FC: 1000 unit/ml) (Non-Patent Document 3)
4: M-CSF (FC: 25 ng/ml)
5: M-CSF (FC: 25 ng/ml)+plant-derived Folch-extracted aqueous phase fraction
6: No Culture
7: No Culture
1-6: Human monocytes, 7: human bone marrow (Human Bone Marrow Marathon-Ready cDNA; Clontech)

Figure 2:
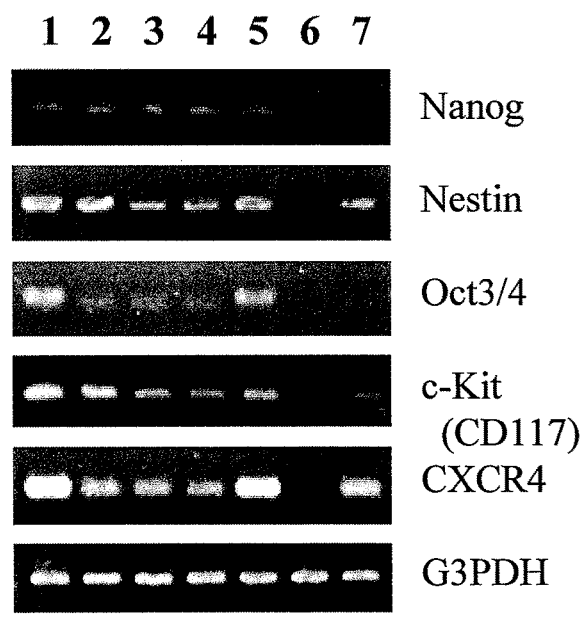
FIG. 2 shows the results of gene expression by RT-PCR.

FIG. 2 shows the results. The results presented in FIG. 2 demonstrated that the stem cells obtained by the present invention (lane 1 or 5) had a very high expression level of CXCR4.

Subsequently, a comparison was made of stem cell-inducing activities of various gangliosides.

Figure 3:
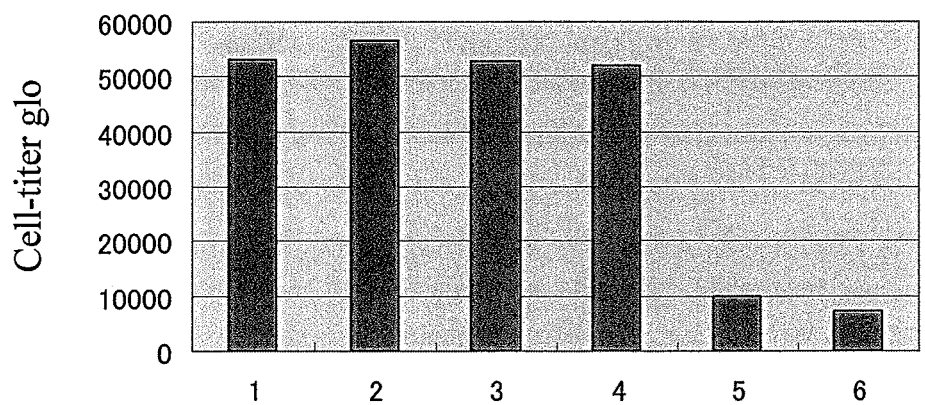
FIG. 3 exhibits the effects of dedifferentiation into stem cells by adding gangliosides.
Figure 4:
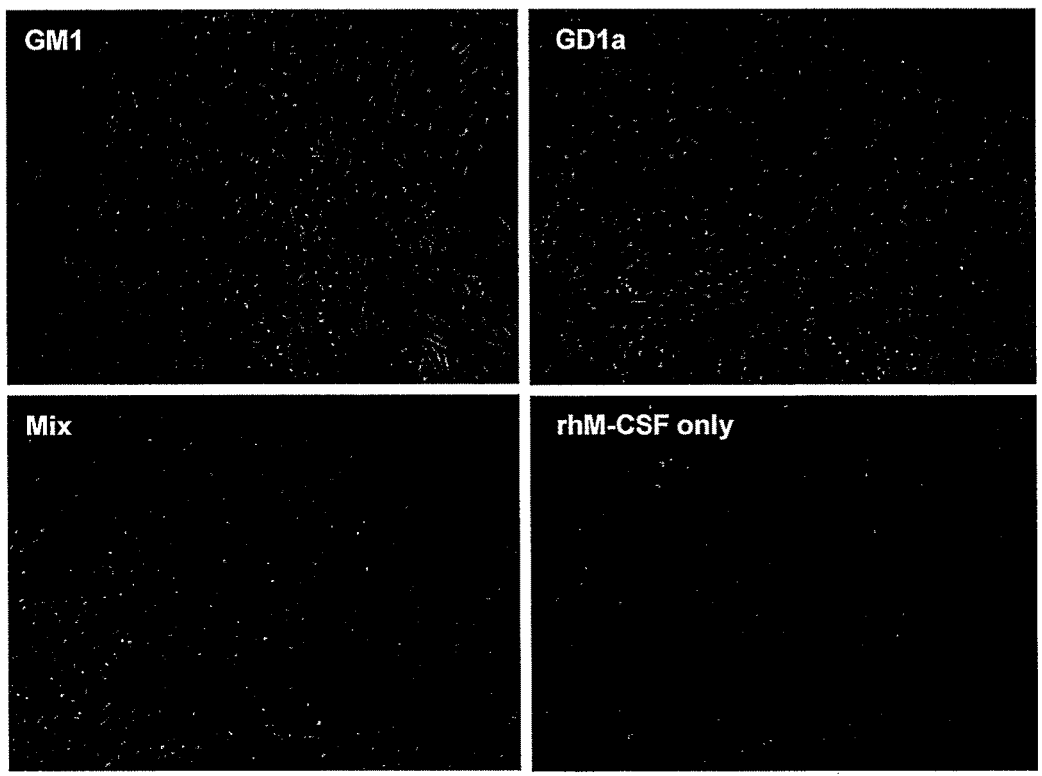
FIG. 4 illustrates cell forms after the addition of gangliosides.

More specifically, gangliosides were added to a culture medium at a final concentration of 100 µg/ml, and peripheral blood monocytes were cultured.

rhM-CSF was added thereto at a final concentration of 25 ng/ml. Then, the number of viable cells in the second week of culture was quantified as luciferase activity using CellTiter-Glo (Promega). Cultures using GM1, GD1a, GT1b, and a mixture thereof all showed equally-strong stem cell-inducing activities in the results (FIG. 3). Moreover, no difference in cell morphology was observed (FIG. 4; the photographs illustrate the cell morphology in the second week of culture).

Figure 5:
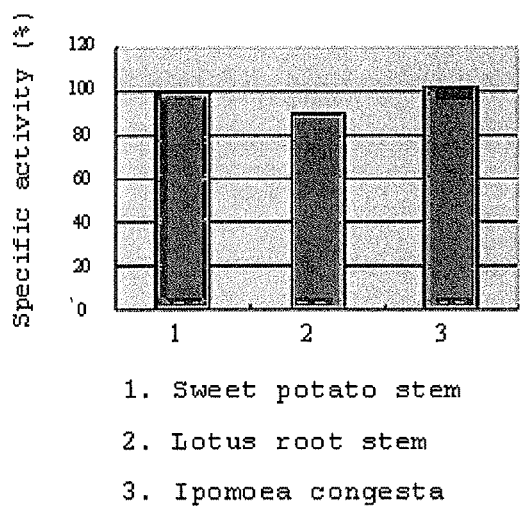
FIG. 5 indicates the dedifferentiation-inducing activity of each plant-extracted fraction.

The lane structures in FIG. 3 are as follows (concentrations are expressed as the final concentration; hereinafter refereed to as "FC"):
1: GM1 (FC: 25 ng/ml)
2: GD1a (FC: 25 ng/ml)
3: GT1b (FC: 25 ng/ml)
4: Mixture of equal amounts of GM1, GD1a, and GT1b (FC: 25 ng/ml (total concentration))
5: Only M-CSF
6: Only plasma Stem Cell-Inducing Activities of Various Plant-Derived Extracts Extracts from stems of a lotus root and *Ipomoea congesta* were both obtained under the same conditions as in that from the stem of the above sweet potato. The comparison of the activities was standardized on the basis of the dry weights of the plants used for extraction. Specific activity is based on the cell proliferative activity of the sweet potato stem extract as 100. As is clear from FIG. 5, similar stem cell-inducing activities were observed in the extracts from the stems of the lotus root and *Ipomoea congesta*.

One feature of the active ingredient of water-soluble plant extract is to be mainly extracted into an aqueous phase by the Folch extraction method. The water-soluble plant extract can be fractionated, separated or purified by passing through various columns. The active ingredient is characterized by binding to anion exchange resins (Q-Sepharose, DEAE-Sepharose, etc.) and lectin-binding resins (Con A etc.) in a wide pH range.

Figure 6:
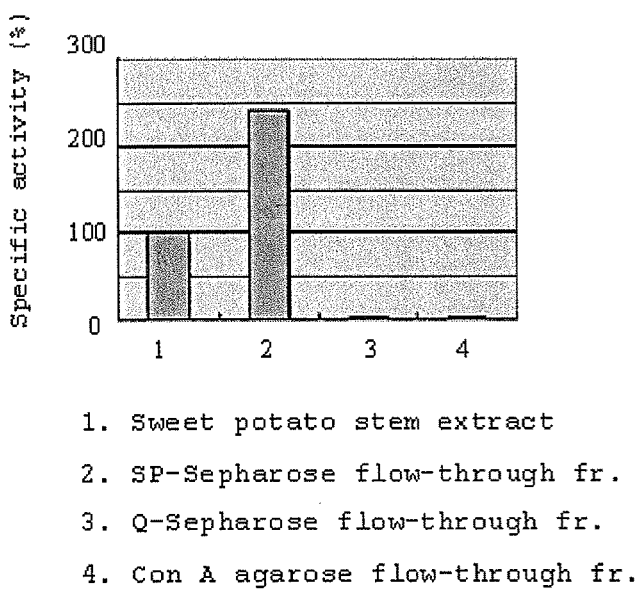
FIG. 6 shows the results of the activity of fractions of sweet potato stem extract-derived dedifferentiation-inducing component obtained by chromatographies.

FIG. 6 shows the results of evaluating the activity of flow-through fractions after applying the extracts to resins having a binding affinity to the active ingredient. The results revealed that the flow-through fractions lost activity because of the binding of the active ingredient to an anion exchange resin and Con A agarose. The results also suggest that an inhibitor was removed by means of a cation exchange resin, thereby raising the activity.

The calculation was based on the activity of the sweet potato stem extract as 100. The increased activity in the flow-through fraction of the cation exchange resin indicates the removal of an inhibitor. The flow-through fractions of the anion exchange resin and lectin Con A resin lost activity, suggesting the retention of the active factor.

Example 2

Healing Effect in Stem Cell-Administered Animal Model (Example of Therapeutic Trial Using Liver Cirrhosis Model Mouse)

Carbon tetrachloride (1 ml/kg (body weight)) was administered to laboratory mice twice a week for 12 consecutive weeks to induce liver cirrhosis artificially. The human monocyte-derived dedifferentiated stem cells (hMDDSC) of the present invention were administered twice to the liver cirrhosis model mice via the tail vein (second administration was conducted one week after the first administration; $1\times10^5$ cells per individual). One week after the second administration (two weeks after the first administration), the liver was extracted from each mouse; and pathological and biochemical analysis of the tissue sections was performed. In hepatitis induced by carbon tetrachloride, SDF1 (Stromal cell derived factor-1) is reportedly expressed highly in the inflamed area as in viral hepatitis (Jung et al., 2006). Since the hMDDSC of the present invention highly expresses CXCR4, which is a receptor for SDF1, the hMDDSC is expected to accumulate in the inflamed area through a bond between the hMDDSC and CXCR4 to exert a healing effect on the surrounding tissues (Kollet et al., 2003; Nervi et al., 2006).

With respect to the liver function detected by blood markers, GOT and GPT values declined immediately and returned to normal levels after carbon tetrachloride administration was completed. Accordingly, these values showed almost normal levels after a two-week curative treatment, and no large differences were observed in the measured values among the test groups. However, as shown below, the 12-week drug treatment caused severe fibrosis in the liver tissue, resulting in liver cirrhosis. The hMDDSC of the present invention had a dramatic effect on the reduction and removal of the fibrous tissue grown in the liver.

1. HISTOPATHOLOGICAL ANALYSIS

Figure 7:
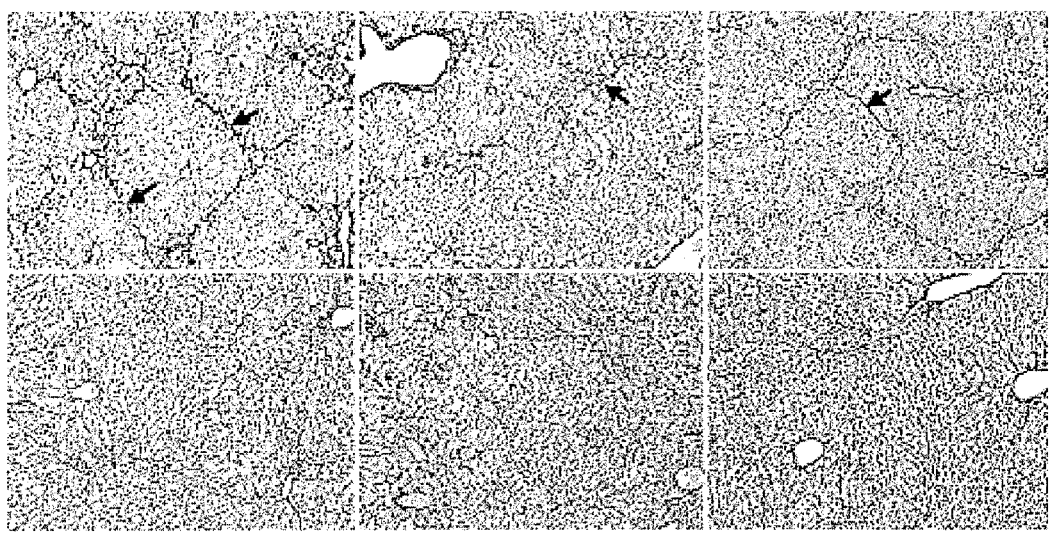
FIG. 7 presents the images of stained anti-collagen antibodies in mouse liver tissue.

Paraffin sections were produced from the extracted and immobilized mouse liver, and collagen fibers, which are an anti-collagen I antibody and the main component of fibrous structure, were detected (FIG. 7, dark brown). At the same time, the nucleus was stained blue (hematoxylin stain).

The upper images show three examples of a control group in which a saline solution was administered, but hMDDSC was not administered, after the induction of liver cirrhosis, and the lower images show three examples in which hMDDSC was intravenously administered twice. The administration of hMDDSC resulted in the obvious removal of thick fiber bundles (indicated by arrows in the upper images) detected by anti-collagen antibodies.

Additionally, Azan-Mallory staining was performed on the same liver sections, and the area of the blue-stained fibrous tissue portion was calculated using an image-analysis microscope (Keyence BZ-9000) (Table 1).

TABLE 1

Results of analyzing images of fibrous portions stained by Azan-Mallory staining

|  | Saline | hMDDSC | Normal |
|---|---|---|---|
| SE | 16131.3 | 1813.4 | 1351.31 |
| Blue pixels | 40006.1 | 30676.7 | 5718 | n = 7, 1400000 pixels/full frame

The hMDDSC-administered group (hMDDSC) showed a value more than 5 times higher than that of the normal control group (Normal) to which carbon tetrachloride was not administered; however, the amount of fibrous tissue in the hMDDSC-administered group decreased as much as 23% compared to that of the physiological saline-administered group (Saline).

2. BIOCHEMICAL ANALYSIS

A) Pro-Collagen Type III Peptide

The blood level of pro-collagen type III peptide was measured in a liver cirrhosis treatment experiment using a similar mouse model. Pro-collagen type III peptide (PIIIP) is a terminal peptide present in a collagen precursor and is free in the blood and tissue as peptide after being digested during collagen production. PIIIP is therefore used as a marker reflecting the production of collagen (Giannini et al., 2001). Blood was extracted from the mouse tail immediately after the two-week treatment experiment, and PIIIP in plasma was measured by the ELISA method (CUSABIO CSB-E08095) (Table 2).

TABLE 2

Amount of pro-collagen type III peptide in blood

|  | Saline | hMDDSC | Normal |
|---|---|---|---|
| ng/mL (plasma) | 283.5 | 64.2 | 57.45 |
| SE | 144 | 24.15 | 29.1 | n = 7

The control group (Saline) to which a physiological saline solution was administered after the induction of liver cirrhosis showed a value about five times higher than the normal control group (Normal), while the amount of pro-collagen in the blood indicated a dramatic decrease due to administration of hMDDSC; a value close to that of a healthy mouse was attained. Because the physiological saline-administered group attained a high value, unusually high production of collagen molecules presumably continued long after the induction of liver cirrhosis by carbon tetrachloride stimulus was stopped. It is found that, however, the unusually high collagen production was immediately suppressed by the administration of hMDDSC, and the amount of pro-collagen in the blood decreased to almost normal levels.

B) Hydroxyproline

For the purpose of quantifying the total amount of fiber in the liver tissue directly from the tissue, the content of hydroxyproline, which is a constituent of collagen, in the liver tissue was measured. The liver extracted from a mouse after a two-week curative treatment was broken and homogenized, and the contained protein was decomposed by a sodium hydroxide treatment. The hydroxyproline concentration was measured by the hydroxyproline-specific color reaction of Chloramine-T and dimethylaminobenzaldehyde (Table 3, Reddy et al., 1996).

TABLE 3

Amount of hydroxyproline in liver tissue

|  | Saline | hMDDSC | Normal |
|---|---|---|---|
| μg/(g) liver | 884.4 | 684 | 222 |
| SE | 90.2 | 67.0 | 8.4 | n = 7

Although the hMDDSC-administered group (hMDDSC) still showed an extremely high value, which was three times higher than that of the normal control group (Normal), it showed as much as a 22.6% decrease compared to the physiological saline-administered group (Saline). In other words, an improvement of liver fibrosis was detected in the hMDDSC-administered group.

After a Folch-extracted aqueous phase fraction of sweet potato stem was administered to the above liver cirrhosis mice via the tail vein in an amount of 6.6 mg/kg, the inventors confirmed that the liver cirrhosis was reduced.

3. CONCLUSION

Thus, the treatment of liver cirrhosis mouse models using the hMDDSC of the present invention is characterized in that fiber production is significantly suppressed and fibrous tissue is removed or reduced by a simple and short-term treatment (only two administrations in two weeks). As a result, it is effective for prompt relief from liver cirrhosis and for restoration of liver tissue to normal liver tissue. Thus, this treatment is an innovative therapeutic system that promotes liver regeneration.

4. CITED DOCUMENTS

Jung Y J, Ryu K H, Cho S J, Woo S Y, Seoh J Y, Chun C H, Yoo K, Moon I H, and Han H S. "Syngenic bone marrow cells restore hepatic function in carbon tetrachloride-induced mouse liver injury", Stem Cells Dev., 2006, 15, 687-695

Kollet O, Shivtiel S, Chen Y Q, Suriawinata J, Thung S N, Dabeva M D, Kahn J, Spiegel A, Dar A, Samira S, Goichberg P, Kalinkovich A, Arenzana-Seisdedos F, Nagler A, Hardan I, Revel M, Shafritz D A, Lapidot T. "HGF, SDF-1, and MMP-9 are involved in stress-induced human CD34+ stem cell recruitment to the liver", J Clin Invest. 2003, 112, 160-169.

Nervi B, Link D C, DiPersio J F. "Cytokines and hematopoietic stem cell mobilization. J Cell Biochem", 2006, 99, 690-705.

Giannini E, Caglieris S, Ceppa P, Risso D, Lantieri P B, Testa R. "Serum pro-collagen III peptide levels are related to lobular necrosis in untreated patients with chronic hepatitis C", Eur J Gastroenterol Hepatol. 2001, 13, 137-141.

Reddy G K, Enwemeka C S. "A simplified method for the analysis of hydroxyproline in biological tissues", Clin Biochem. 1996, 29, 225-229.

The invention claimed is:

1. A method of producing stem cells, comprising culturing monocytes in the presence of (i) M-CSF and (ii) at least one member selected from the group consisting of 1-100 μg/ml of ganglioside and a plant-derived Folch-extracted aqueous phase fraction.

2. The method according to claim 1 wherein the culture is performed for 7 to 14 days.

3. The method of producing stem cells according to claim 1, wherein ganglioside is at least one number selected from the group consisting of GD1a, GD1b, GD2, GD3, GM1, GM2, GM3, GT1b, and GQ1b.

4. The method of producing stem cells according to claim 2, wherein ganglioside is at least one number selected from the group consisting of GD1a, GD1b, GD2, GD3, GM1, GM2, GM3, G1ib, and GQ1b.

* * * * *